US008765192B2

(12) United States Patent
Lichtenstein

(10) Patent No.: US 8,765,192 B2
(45) Date of Patent: Jul. 1, 2014

(54) WEIGHT REDUCTION SYSTEM AND METHOD

(76) Inventor: Joseph Lichtenstein, Brooklyn, NY (US)

( * ) Notice: Subject to any disclaimer, the term of this patent is extended or adjusted under 35 U.S.C. 154(b) by 381 days.

(21) Appl. No.: 12/951,039

(22) Filed: Nov. 20, 2010

(65) Prior Publication Data

US 2012/0128806 A1 May 24, 2012

(51) Int. Cl.
*A61K 36/81* (2006.01)
*A61K 36/00* (2006.01)

(52) U.S. Cl.
USPC ............................ 424/725; 424/773; 424/777

(58) Field of Classification Search
USPC ......................................... 424/725, 777, 773
See application file for complete search history.

(56) References Cited

U.S. PATENT DOCUMENTS

| 3,135,098 | A | * | 6/1964 | Root | 405/186 |
|---|---|---|---|---|---|
| 5,137,508 | A | * | 8/1992 | Engman | 602/79 |
| 5,326,685 | A | * | 7/1994 | Gaglio et al. | 433/215 |
| 6,353,145 | B1 | * | 3/2002 | Church | 602/48 |
| 7,396,976 | B2 | * | 7/2008 | Hurwitz et al. | 602/58 |
| 2002/0068891 | A1 | * | 6/2002 | Weathers | 602/48 |
| 2003/0036716 | A1 | * | 2/2003 | Knutson et al. | 602/43 |
| 2005/0261654 | A1 | * | 11/2005 | Swanson | 604/385.06 |
| 2008/0139988 | A1 | * | 6/2008 | Dayan et al. | 602/48 |
| 2009/0000002 | A1 | * | 1/2009 | Hadash | 2/16 |

FOREIGN PATENT DOCUMENTS

| JP | 2000254160 A | * | 9/2000 |
|---|---|---|---|
| JP | 2002028250 A | * | 1/2002 |
| JP | 2003052734 A | * | 2/2003 |

OTHER PUBLICATIONS

Allison et al. Alternative Treatments for Weight Loss: A Critical Review; Critical Reviews in Food Science and Nutrition 41.1 (2001): 1.*
Cavender, A. Folk Medicine in Southern Appalachia; The University of North Carolina Press, USA, 2003, p. 102.*
Cooke et al. 'The Obesity Pipeline: Current Strategies in the Development of Anti-obesity Drugs,' p. 919, col. 1.*
Jensen, B: Foods That Heal; Penguin Putnam Inc. New York, NY 1993, p. 222.*

* cited by examiner

*Primary Examiner* — Patricia Leith
(74) *Attorney, Agent, or Firm* — Harvey Lunenfeld

(57) ABSTRACT

A method of topically applying natural plant product for dissipation of human adipose tissue, comprising: (a) topically applying an inner portion of a natural plant product to an epidermal layer exterior to adipose tissue to be dissipated of a user's body for a period of time, upon which a percentage of the adipose tissue softens and dissolves, thus, reducing the adipose tissue of the user's body; (b) removing the topically applied inner portion of the natural plant product from the epidermal layer for another period of time; (c) repeating steps (a) and (b); and weight reduction apparatus comprising a topical applicator having a receiving container adapted to removably receive a natural plant product and having an opening or a porous wall adapted to facilitate pulp, juices, and/or extracts of the natural plant product to contact a user's epidermal layer exterior to the adipose tissue to be dissipated.

21 Claims, 17 Drawing Sheets

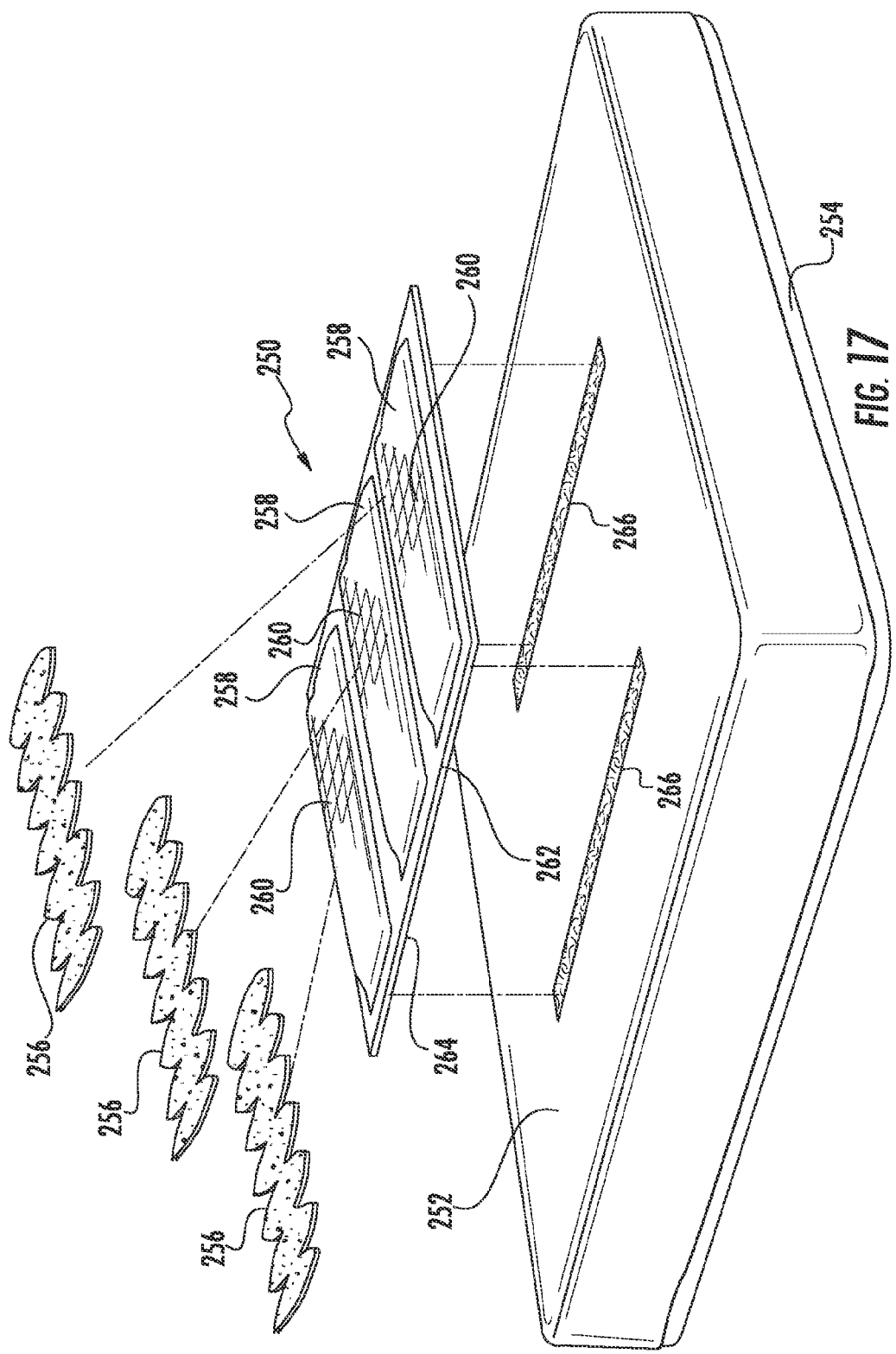

WEIGHT REDUCTION SYSTEM AND METHOD

BACKGROUND OF THE INVENTION

1. Field of the Invention

The present invention relates generally to weight reduction systems and more particularly to topical plant matter human weight reduction systems.

2. Background Art

Human overweight and obesity are generally considered to be medical conditions in which human body fat accumulates to the level that it may have an adverse impact on health, exacerbate and create increased health problems, and result in reduced life expectancy. Human weight reduction and the loss of undesired body fat is a goal of many individuals in today's society, in order to maintain a healthy body and an attractive appearance to those around us, and improve one's quality of life.

Weight reduction goals often include the reduction of body fat to acceptable levels, which can be related to body mass index, and, which in turn, is related to an individual's weight and height, and evaluated in conjunction with an individual's age, sex, and body frame size.

The primary treatment of obesity and human overweight are often dieting, physical exercise, appetite reducing drugs, and, in sever instances, surgery. However, other alternatives that allow an individual to remove excess fat by topical application of a natural product and/or biodegradable product are needed. The natural product and/or biodegradable product should be easy to obtain and an individual should be capable of topically applying the product at his or her own leisure in the privacy of his or her home and/or under his or her clothing, allowing the individual to have the natural product and/or biodegradable product applied during normal daily activities.

Different weight reduction systems and methods have heretofore been known. Such weight reduction systems and methods often include attempting to modulate an individual's weight through dieting, consumption of a variety of ingestible food and beverage products, drugs and pharmaceuticals, ingestible herbal products, exercise programs, and/or calorie counting methods. However, none of the weight reduction systems and methods adequately satisfies these aforementioned needs.

U.S. Pat. No. 6,210,702 (Samman) discloses a weight loss composition and method for losing weight that relates to a dieting method and line of food products that replace similar food products and are utilized by a dieting method to induce a slowed carbohydrate absorption rate thereby achieving weight loss. The dieting method is used to induce a high satiating effect to control eating habits, and provide a dieter with additional doses of mono and poly unsaturated fatty acids to prevent decreased energy consumption.

U.S. Pat. No. 6,635,015 (Sagel) discloses a body weight management system that may be used for humans and domestic animals. The body weight management system utilizes devices and compositions to shift energy balance of a user, such that the calories burned the user are greater than the calories consumed by the user. The devices include a diet-tracking system, devices for estimating energy expenditure of the subject and a satiety agent, and may be used for body weight maintenance, weight reduction or gain, reduction of body fat, gain of muscle mass, and improvement of a subject's fitness.

U.S. Pat. No. 7,098,029 (Belyea, et al.) discloses a product and method for control of obesity, which relate to food and beverage products that may be used for control of obesity. The food and beverage products comprise or are made of a transgenic plant or parts thereof, comprising a nucleic acid molecule, the nucleic acid molecule encoding a C-terminal growth hormone fragment, which has the ability to modulate lipid metabolism. The transgenic plant may be used in production of a fermented food or beverage product, or may be a part of an edible plant, such as a fruit or vegetable, including but not limited to tomato, banana, and potato.

U.S. Pat. No. 7,476,406 (Smidt) discloses a multifaceted weight control system, in which weight-controlling or modulating compositions, systems, and methods are described. Such compositions may include a thermogenic ingredient, a cortisol modulating ingredient, and a carbohydrate craving controlling ingredient. Furthermore, such compositions may be used in connection with exercise and dietary modifications or restrictions.

U.S. Pat. No. 7,109,198 (Gadde, et al.) discloses a method for treating obesity, and, in particular, a method of treating obesity and minimizing metabolic risk factors associated therewith, using, for example, zonisamide or other weight-loss promoting anticonvulsant either alone or in combination with bupropion or other compound that enhances the activity of norepinephrine and/or dopamine via uptake inhibition or other mechanism.

Different cellulite reduction systems and methods have heretofore been known. However, none of the cellulite reduction systems and methods adequately satisfies these aforementioned needs.

U.S. Pat. No. 5,051,449 (Kligman) discloses treatment of cellulite with retinoids, including a method for retarding and reversing cellulite comprising topically applying to human skin a retinoid in an amount and for a period of time effective to retard or reverse cellulite, where the amount is insufficient to be excessively irritating. The method preferably uses retinoic acid in an emollient vehicle.

Different muscle mass enhancing systems and methods have heretofore been known. However, none of the muscle mass enhancing systems and methods adequately satisfies these aforementioned needs.

United States Patent Application Publication 2007/0207226 (Mowrey, et al.) discloses a composition for enhancing muscle mass development in animals. Compositions containing nicotine and/or nicotinic acetylcholine receptor agonists are provided for administration in therapeutically effective amounts to enhance muscle development in animals, the nicotine and/or nicotinic acetylcholine receptor agonists being particularly derived from natural sources that produce beneficially high amounts of nicotine and/or nicotinic acetylcholine receptor agonists which are also well-tolerated and ingestible for the intended purpose.

Different skin preparations have heretofore been known. Such skin preparations include compositions for treatment of aging skin and dermatological disorders. However, none of the skin preparations adequately satisfies these aforementioned needs.

U.S. Pat. No. 7,435,432 (Olson) discloses combined marine and plant extract compositions, in which a composition comprising cartilage extract, grape seed extract and tomato extract was found to have an anti-oxidant effect and free-radical inhibition. The tomato extract comprises lycopene. The composition, which comprises a hydrophilic antioxidant, a lipophilic (hydrophobic) antioxidant, and a cartilage extract increases collagen synthesis in the dermis. Furthermore, the composition lowers collagenase activity and levels of advanced glycation end products (AGE). The signs of ageing, such as photoageing due to exposure to UV radiation, are related to the levels of collagen syntheses and free-radical oxidation. Compositions of the invention are intended for the treatment of ageing skin and the delaying of the onset of the signs of ageing in healthy skin.

U.S. Pat. No. 6,630,163 (Murad) discloses a method of treating dermatological disorders with fruit extracts, which includes administering a therapeutically effective amount of at least one fruit extract in an amount sufficient to neutralize free radicals; and a pharmaceutically acceptable carrier. Preferred fruit extracts include extracts from apricots, apples, peaches, pears, pineapples, papayas, pomegranates, cherries, kiwis, tangerines and oranges. The most preferred extract is extract from pomegranate.

U.S. Pat. No. 7,618,662 (Hines, et al.) discloses use of natural plant extracts in cosmetic compositions, which includes compositions and methods for treating, improving the appearance of skin, particularly, treating, preventing, ameliorating, reducing and/or eliminating loss of subcutaneous fat in the skin, wherein the compositions include natural plant constituents that stimulate lipid synthesis. The plant extracts are preferably derived from *Rhinacanthus nasutus, Humulus scandens, Sesbania grandiflora, Amorphophallus campanulatu, Pouzolzia pentandra*, and *Piper betel*, and any combinations thereof. The compositions are preferably applied to the skin, or are delivered by directed means, to a site in need thereof.

U.S. Pat. No. 7,592,024 (Ptchelintsev, et al.) discloses topical compositions containing melicope hayselii and a method of treating skin, which include cosmetic compositions comprising an extract of *Melicope hayesii* and methods of using such compositions to impart anti-aging benefits to the skin are disclosed. These compositions are believed to have modulatory activity against at least one biochemical pathway implicated in skin aging.

U.S. Pat. No. 6,989,150 (Golz-Berner, et al.) discloses cosmetic preparation of active substances with a synergistically increased radical protection factor. The cosmetic preparation of active substances, as in combination with other active substances, protects the skin against free radical aggression in a particularly effective manner. The preparation includes a bark extract of quebracho blanco, which contains at least 90 wt. % of proanthocyanidine oligomers, a silkworm extract, which contains the peptide cecropine, amino acids and a vitamin mixture, a non-ionic, cationic or anionic hydro-gel, phopholipids, a yeast disintegration product, and cyclodextrines. The preparation can contain additional active substances, such as plant extracts of acerola, sea weed, citrus, bitter orange, cherry, papaya, tea, coffee beans, skin tree and angelica. The preparations have synergistically increased radical protection factors of up to 10,000. Cosmetic compositions containing the preparations have radical protection factors of between 40 and 400 according to the portion of the preparation.

U.S. Pat. No. 7,780,995 (Berardesca) discloses a composition based on natural extracts for the prevention and treatment of cutaneous ageing and particularly wrinkles, which comprises in combination: leucocyanadines in the form of extract of *Vitis vinifera*; triterpenes in the form of an extract of *Centella asiatica*; fish cartilage extract.

Different fruit conformable resiliently compressible force absorption systems have been known.

U.S. Pat. Nos. 7,303,076 and 7,377,392 (Scalise) disclose a fruit conformable resiliently compressible force absorption system that includes a fruit protection and transportation system. Apparatus and methods to absorb impact and compression forces to reduce damage to fruit are shown. Particular embodiments of the invention comprise a fruit protector blank of resiliently compressible force absorption material, having a substantially planar surface that can be conformed to a portion of an exterior surface of various kinds of fruit. Other embodiments provide a molded force absorption cover of resiliently compressible foam material that elastically conforms to a portion of an exterior surface of a fruit.

For the foregoing reasons, there is a need for a weight reduction system and method and more particularly to a topical plant matter human weight reduction system and method. The weight reduction system and method should include the use of a natural product, natural plant product, and/or biodegradable product that is easy to obtain and that an individual be capable of topically applying the product at his or her own leisure in the privacy of his or her home and/or under his or her clothing, allowing the individual to have the natural product and/or biodegradable product applied during normal daily activities. The weight reduction system and method should be simple to use in a quick, convenient, and efficient manner, and should use easily obtainable natural plant products, natural products, and/or biodegradable products, which may be topically applied to an in individual. The weight reduction system should be durable, light weight, inexpensive, safe to use, attractive, sturdy, easy to use, and of simple construction.

SUMMARY

The present invention is directed to a weight reduction system and method and more particularly to a topical plant matter human weight reduction system and method. The weight reduction system and method includes the use of a natural product, natural plant product, and/or biodegradable product that is easy to obtain. An individual is capable of topically applying the product at his or her own leisure in the privacy of his or her home and/or under his or her clothing, allowing the individual to have the natural product and/or biodegradable product applied during normal daily activities. The weight reduction system and method is simple to use in a quick, convenient, and efficient manner, and uses easily obtainable natural plant products, natural products, and/or biodegradable products, which may be topically applied to the individual. The weight reduction system is durable, light weight, inexpensive, safe to use, attractive, sturdy, easy to use, and of simple construction.

A method for weight reduction using a natural plant product having features of the present invention comprises at least the following steps: (a) topically applying an inner portion of a natural plant product to an epidermal layer exterior to adipose tissue to be dissipated of a user's body for a period of time, upon which a percentage of the adipose tissue to be dissipated softens and dissolves, thus, reducing the adipose tissue of the user's body; (b) removing the topically applied inner portion of the natural plant product from the epidermal layer exterior to the adipose tissue to be dissipated for another period of time; (c) repeating steps (a) and (b), as required to further reduce the adipose tissue of the user's body, as required.

A weight reduction apparatus having features of the present invention comprises a topical applicator, comprising a receiving container adapted to removably receive a natural product, natural plant product, and/or biodegradable product therein and having a porous wall adapted to facilitate pulp, juices, and/or extracts of the natural product, natural plant product, and/or biodegradable product to contact a user's epidermal layer exterior to adipose tissue to be dissipated.

DRAWINGS

These and other features, aspects, and advantages of the present invention will become better understood with regard to the following description, appended claims, and accompanying drawings where:

FIG. 17 is a perspective view of an alternate embodiment of a weight reduction apparatus.

DESCRIPTION

Figure 1:
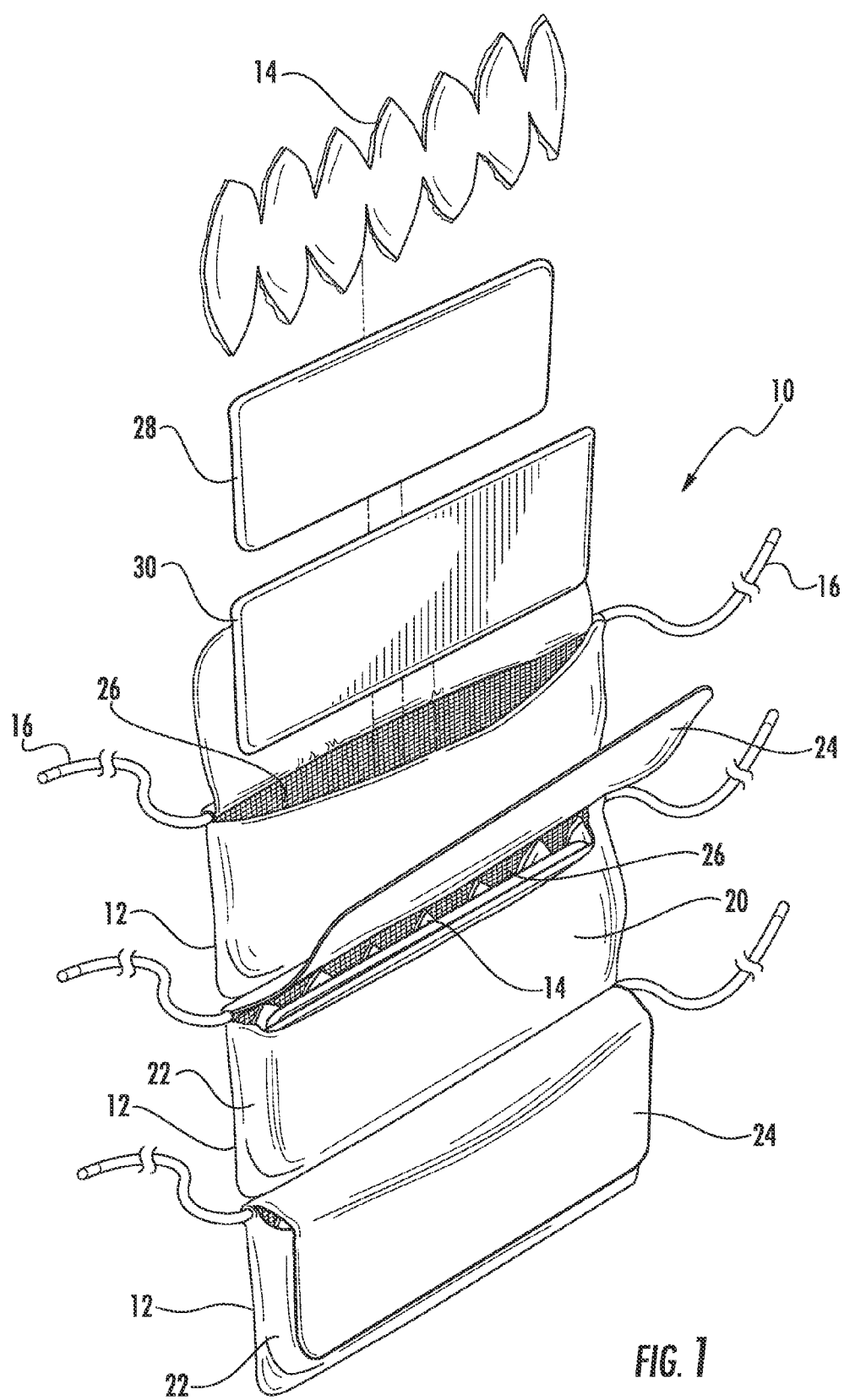
FIG. 1 is a partially exploded perspective view of a weight reduction apparatus, constructed in accordance with the present invention, showing a natural plant product for insertion into the weight reduction apparatus.

The preferred embodiments of the present invention will be described with reference to FIGS. 1-17 of the drawings. Identical elements in the various figures are identified with the same reference numbers.

Various poultices that use natural plant products have been known, including, in particular, tomato, which has been known for its healing powers. Such poultices often include a soft, moist mass of cloth, bread, meal, herbs, and the like, typically applied hot or warm as a medicament to the body, and may include natural plant products, such as tomato and/or other fruit and/or vegetables, including potato, which has also been known as a poultice.

Botanically, tomato is a fruit, but by cultivation and use, the tomato is often considered a vegetable. Tomatoes are not only a rich source of lycopene, but are also a source of beta-carotene, alpha-carotene, lutein/zeaxanthin, phytuene/phytofluene, and various polyphenols, and contain small amounts of B vitamins (thiamine, pantothenic acid, vitamin B6, and niacin), as well as folate, vitamin E, magnesium, manganese, and zinc.

Much of the tomato's healing powers can be attributed to lycopene, which the tomato contains, and which is considered to be a major contributor to the beneficial effects of tomatoes. Lycopene is a powerful antioxidant that scavenges a large number of free radicals and quenches the free-radical singlet oxygen, a particularly deleterious form of oxygen.

This inventor has discovered that the application of green tomatoes, potatoes, tomatoes, and other natural products, natural plant products, and/or other biodegradable products are useful in the dissipation of human fat, when applied topically to a human epidermal layer exterior to adipose tissue or body fat to be dissipated for a period of time. The green tomatoes, potatoes, tomatoes, and other natural product, natural plant product, and/or other biodegradable products are preferably topically applied for several hours to the human epidermal layer exterior to the adipose tissue or body fat to be dissipated and then removed for a number of hours, the process being repeated until desired results are achieved.

Green tomatoes, for example, are preferably cut open and the entire inner portions of a plurality of whole green tomatoes are preferably topically applied for several hours to the human epidermal layer exterior to adipose tissue or body fat to be dissipated, then removed for a number of hours, the cut open and previously used green tomatoes being discarded upon removal, the process being repeated with unused green tomatoes, until desired results are achieved. Typical areas that the green tomatoes are preferably topically applied to in humans include the epidermal layer about the abdomen, buttocks, hips, thighs, and other fatty areas. Alternatively, exterior portions of a plurality of whole green tomatoes may be applied to the human epidermal layer exterior to adipose tissue or body fat to be dissipated in the same manner, or a combination of interior portions and/or exterior portions of the whole green tomatoes may be applied, depending upon the needs of the user.

The process of topically applying the green tomatoes, potatoes, tomatoes, and other natural product, natural plant product, and/or biodegradable products for several hours and removing such products for a number of hours from the human epidermal layer exterior to the adipose tissue or body fat to be dissipated is repeated with each topical application being repeated with unused product, until desired results are achieved. Other suitable fruits and/or vegetables may also be used.

A natural plant product may be used for weight reduction by topically applying the natural plant product to a user in steps of a method of the present invention, comprising: (a) topically applying an inner portion of a natural plant product to an epidermal layer exterior to the adipose tissue to be dissipated of a user's body for a period of time, upon which a percentage of the adipose tissue or body fat softens and dissolves, thus, reducing the adipose tissue or body fat of the user's body; (b) removing the topically applied inner portion of the natural plant product from the epidermal layer exterior to the adipose tissue to be dissipated for another period of time; (c) repeating steps (a) and (b), as required to further reduce the adipose tissue of the user's body, as required.

Pulp, juices, and/or extracts of the natural product, natural plant product, and/or biodegradable product are applied to a user's epidermal layer exterior to adipose tissue to be dissipated, using the weight reduction apparatus and method of the present invention.

The pulp, juices, and/or extracts of the natural product, natural plant product, and/or biodegradable product are topically applied to the user's epidermal layer exterior to the adipose tissue to be reduced and/or dissipated and/or adjacent to such areas. As the adipose tissue is reduced and/or dissipates over time, neighboring areas and other areas of adipose tissue are expected to be reduced and/or dissipate and result in an overall reduction of body fat, improvement in the user's health, and reduced arterial and coronary artery disease.

FIGS. 1-17 of the drawings disclose alternate embodiments of weight reduction apparatus of the present invention that may be used for topically applying the natural plant product to a user in the method of the present invention.

Figure 2:
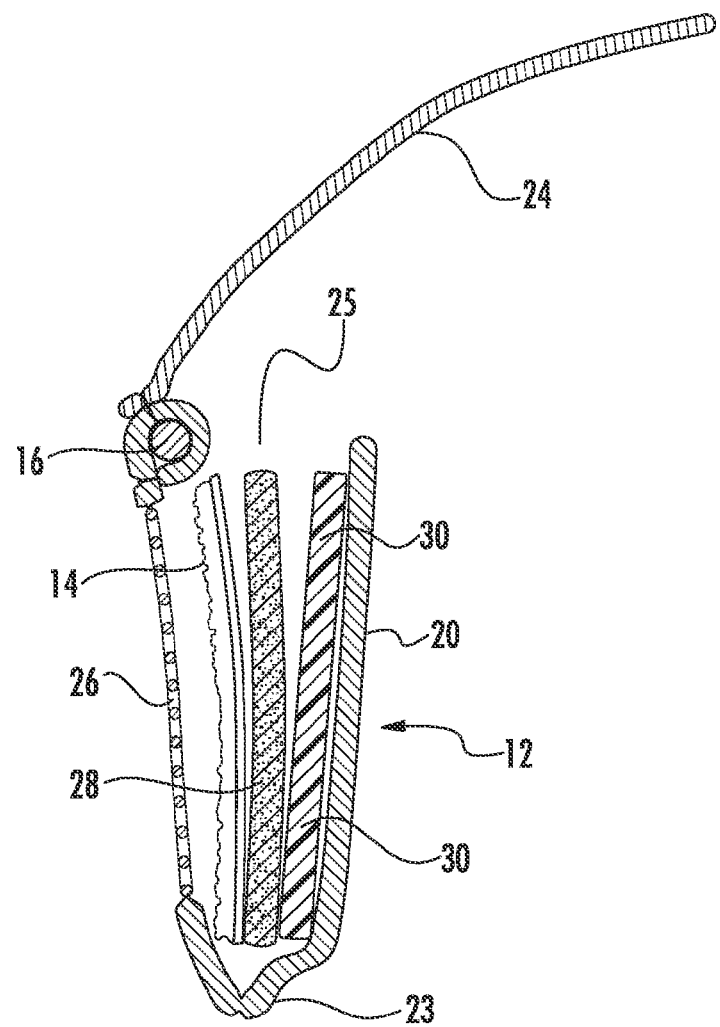
FIG. 2 is a side cross section view of a receiving pocket topical applicator of the weight reduction apparatus and the natural plant product of FIG. 1.
Figure 3:
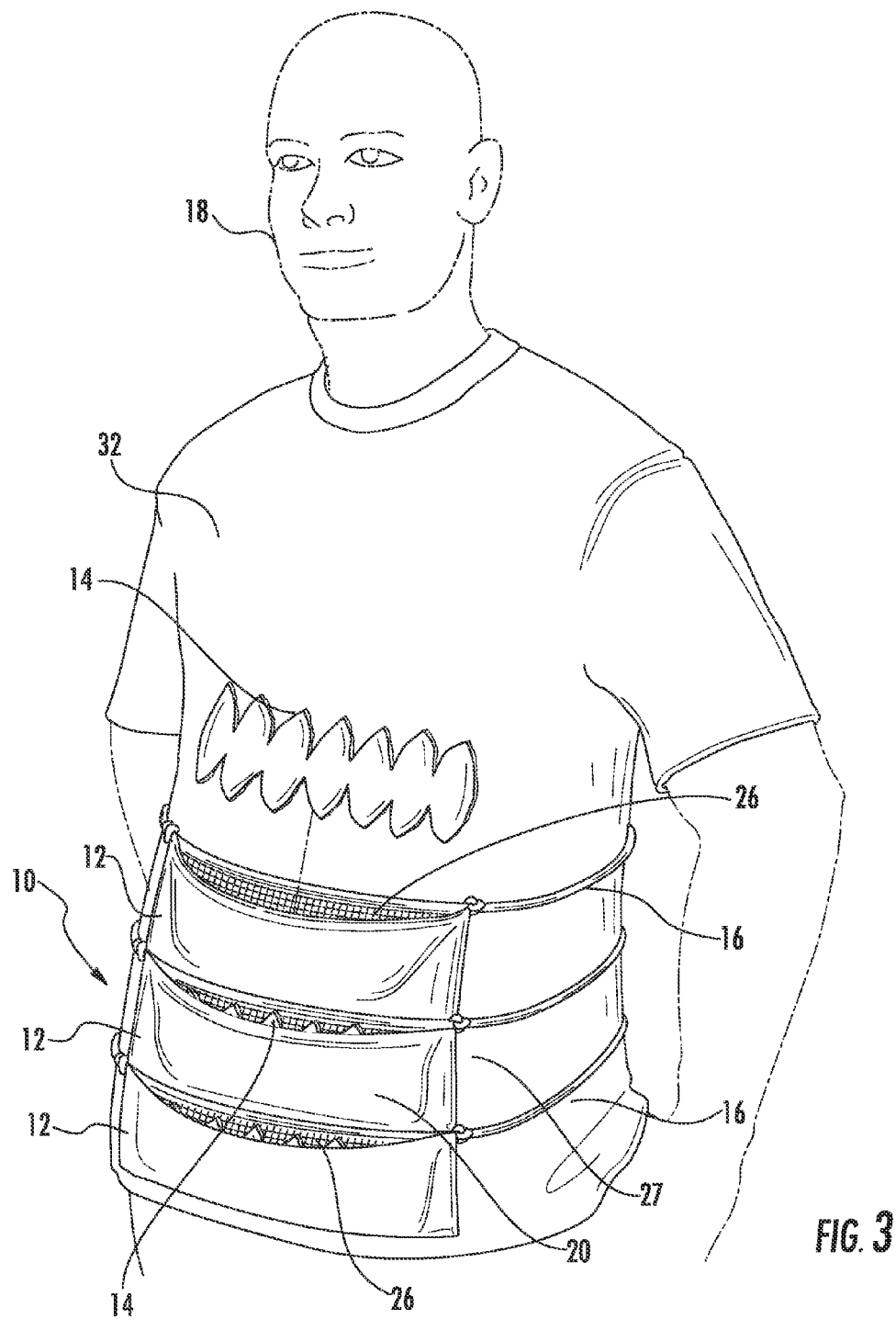
FIG. 3 is a partially exploded and partially cutaway perspective view of the weight reduction apparatus of FIG. 1, worn by a user, shown in phantom, showing the natural plant product for insertion into the weight reduction apparatus.

FIGS. 1-3 show an embodiment of the present invention, a weight reduction apparatus 10 having a plurality of receiving pocket topical applicators 12 for removably receiving a natural plant product 14 and/or other suitable biodegradable weight loss product alone or in combination with one another and a plurality of straps 16 or other suitable fastening means adapted to removably fasten the weight reduction apparatus 10 to a suitable area of a user 18.

Each of the receiving pocket topical applicators 12 has a frontal portion 20, side portions 22, which are integral with the frontal portion 20, a bottom portion 23, which is also integral with the frontal portion 20, a fold-over cover flap 24, an opening 25 adapted to removably receive the natural plant product 14 and/or other suitable biodegradable weight loss product, and a porous rear portion 26, which is typically of gauze-like material, mesh, screen-like material, or other suitable material, which allows the natural plant product 14 and/or other suitable biodegradable weight loss product to leach therethrough and be topically applied to a suitable area of the user 18.

The receiving pocket topical applicators 12 are typically placed about the abdomen 27 of the user 18, although the receiving pocket topical applicators 12 may be placed about another suitable area.

Each of the receiving pocket topical applicators 12 also has a resiliently compressive material 28 adapted to press the natural plant product 14 and/or other suitable biodegradable weight loss product against the porous rear portion 26 and, thus, a suitable area of the user 18, and a suitable waterproof material 30, as shown in FIGS. 1 and 2, adapted to minimize any juices from the natural plant product 14 and/or other suitable biodegradable weight loss product leaching through the frontal portion 20 of the receiving pocket topical applicator 12. The opening 25 is adapted to removably receive the natural plant product 14 and/or other suitable biodegradable weight loss product, the resiliently compressive material 28, and the waterproof material 30.

The weight reduction apparatus 10 may be worn by the user 18 with the porous rear portion 26 in contact with the user 18 or alternatively over a shirt 32, as shown in FIG. 3, or garment or other suitable material that allows the natural plant product 14 and/or other suitable biodegradable weight loss product to leach therethrough and be topically applied to a suitable area of the user 18. The shirt, garment, or other suitable material may be, for example, gauze-like material, mesh, screen-like material, or other suitable material.

The weight reduction apparatus 10 is preferably flexible and of garment like material or other suitable material for the comfort of the user.

Figure 4:
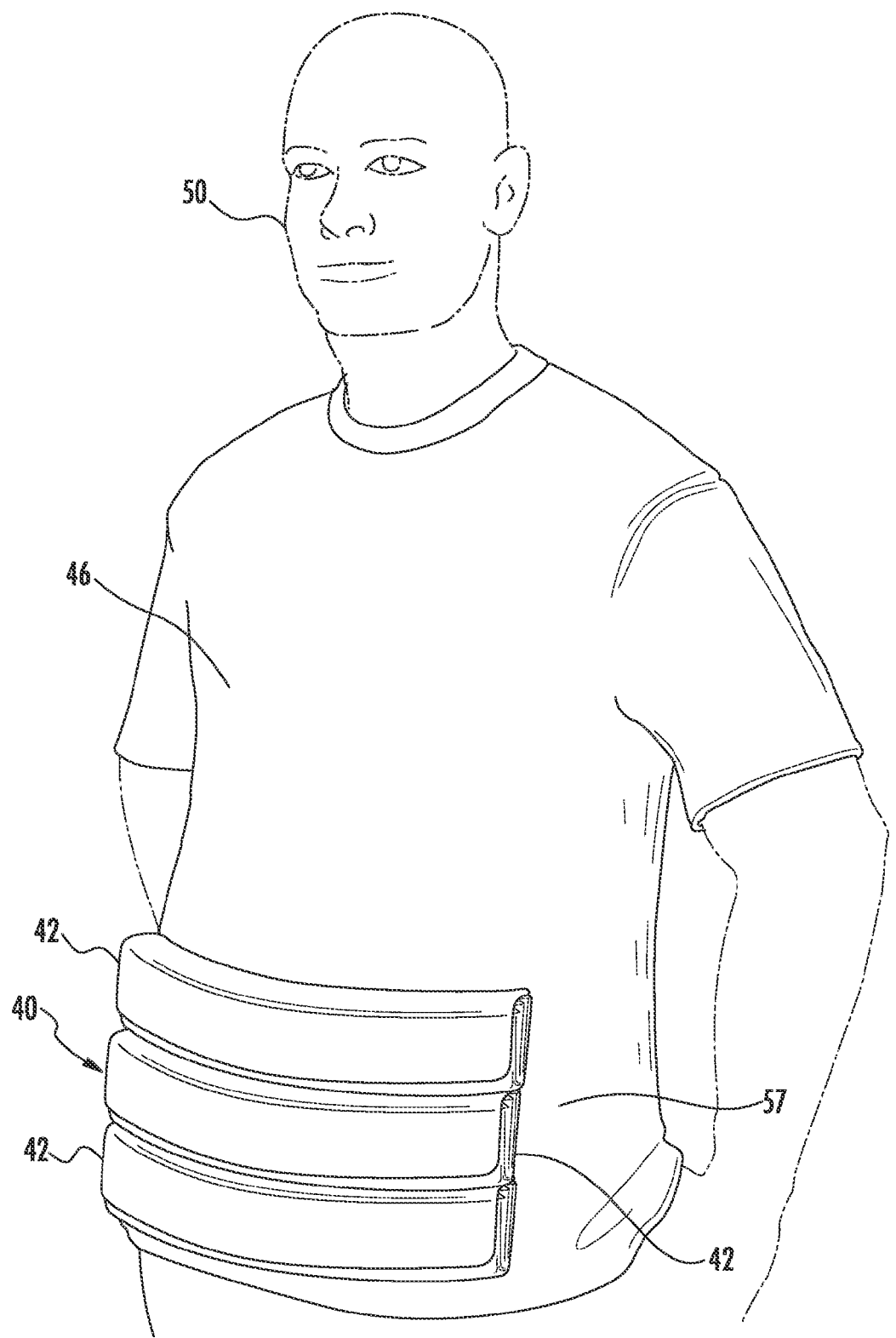
FIG. 4 is a perspective view of an alternate embodiment of a weight reduction apparatus, worn by a user, shown in phantom.
Figure 5:
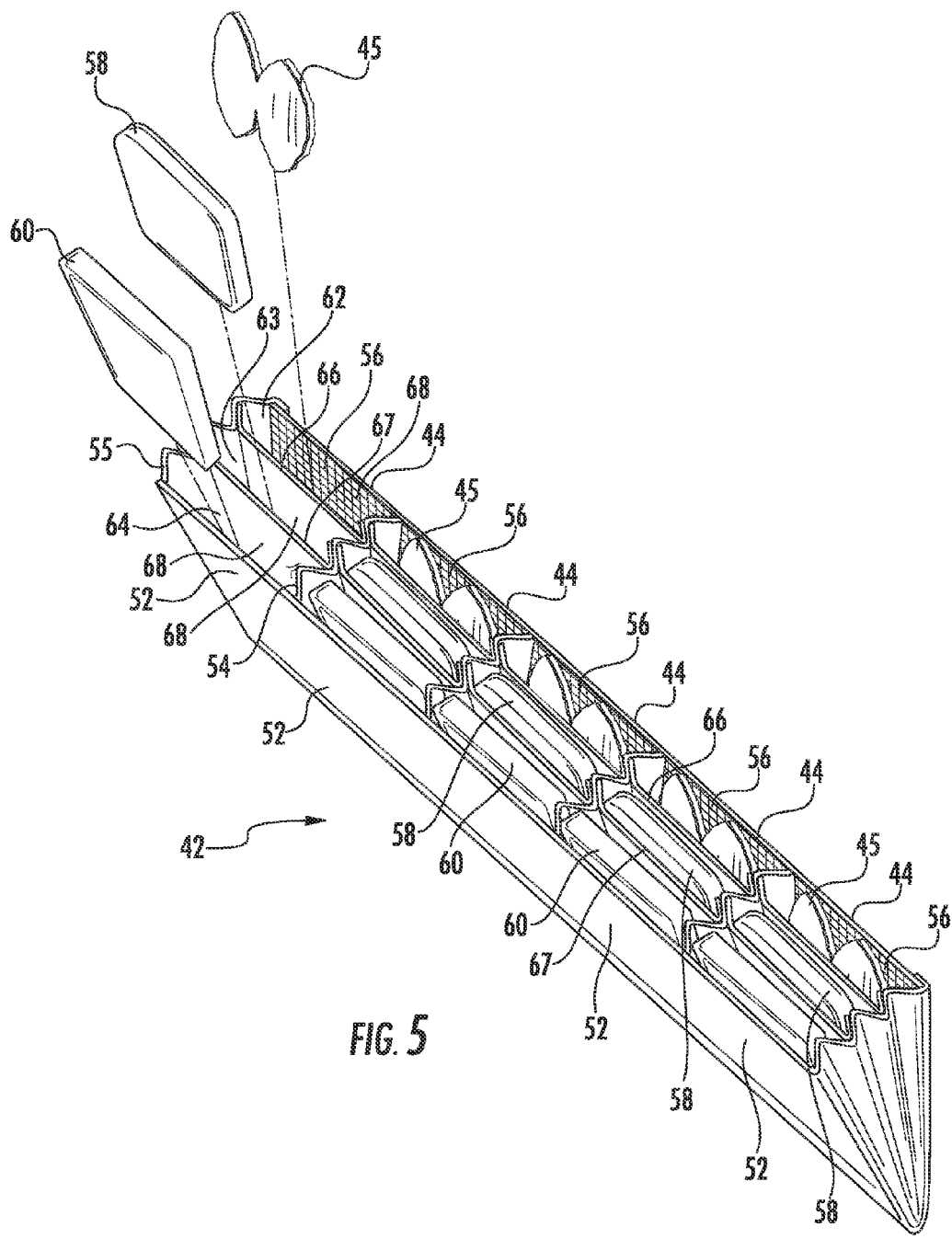
FIG. 5 is a partially exploded perspective cutaway view of a plurality of receiving pocket topical applicators of the weight reduction apparatus of FIG. 4 and a natural plant product for insertion into the receiving pocket topical applicators.

FIGS. 4 and 5 show an alternate embodiment of a weight reduction apparatus 40, which is substantially the same as the weight reduction apparatus 10, except that the weight reduction apparatus 40 has a plurality of receiving pocket topical applicator rows 42, each of which has a plurality of receiving pocket topical applicators 44 adapted to removably receive a natural plant product 45 and/or other suitable biodegradable weight loss product.

The weight reduction apparatus 40 may be an integral part of a shirt 46, as shown in FIG. 4, or garment or other suitable material that allows the natural plant product 45 and/or other suitable biodegradable weight loss product to leach therethrough and be topically applied to a suitable area of user 50. The shirt 46, garment, or other suitable material may be, for example, gauze-like material, mesh, screen-like material, or other suitable material.

Each of the receiving pocket topical applicator rows 42 has the plurality of the receiving pocket topical applicators 44, each of which has a frontal portion 52, side wall portions 54 and 55, and a porous rear portion 56, as shown in FIG. 5, which is typically of gauze-like material, mesh, screen-like material, or other suitable material, which allows the natural plant product 45 and/or other suitable biodegradable weight loss product to leach therethrough and be topically applied to a suitable area of the user 50, in an area such as the abdomen 57, buttocks, hips, thighs, or other suitable areas. The porous rear portion 56 may optionally be an integral portion of the shirt, garment, or other suitable material.

Each of the plurality of receiving pocket topical applicators 44 also has a resiliently compressive material 58 adapted to press the natural plant product 45 and/or other suitable biodegradable weight loss product against the porous rear portion 56 and, thus, a suitable area of the user 50, and a waterproof material 60 adapted to minimize any juices from the natural plant products 45 and/or other suitable biodegradable weight loss products leaching through the frontal portion 52 of the receiving pocket topical applicators 44.

Each of the plurality of receiving pocket topical applicators 44 has a plurality of compartments 62, 63, and 64 adapted to separate or isolate the natural plant product 45 and/or other suitable biodegradable weight loss product from the resiliently compressive material 58 and the waterproof material 60. The compartments 62, 63, and 64 are also adapted to separate or isolate the compressive material 58 and the waterproof material 60 from each other. The resiliently compressive material 58 and the waterproof material 60 are shown in FIG. 5 inserted into the compartments 63 and 64, respectively; however, the resiliently compressive material 58 and the waterproof material 60 may alternatively be inserted into the compartments 64 and 63, respectively, depending upon the needs of the user 50. The compartments 62, 63, and 64 are separated by interior walls 66 and 67 respectively, and have openings 68 adapted to removably receive the natural plant product 45 and/or other suitable biodegradable weight loss product, the resiliently compressive material 58, and the waterproof material 60.

The weight reduction apparatus 40 may alternatively or additionally have a plurality of straps or other suitable fastening means adapted to removably fasten the weight reduction apparatus 40 to a suitable area of the user 50 or to a shirt, garment, or other suitable material.

Figure 6:
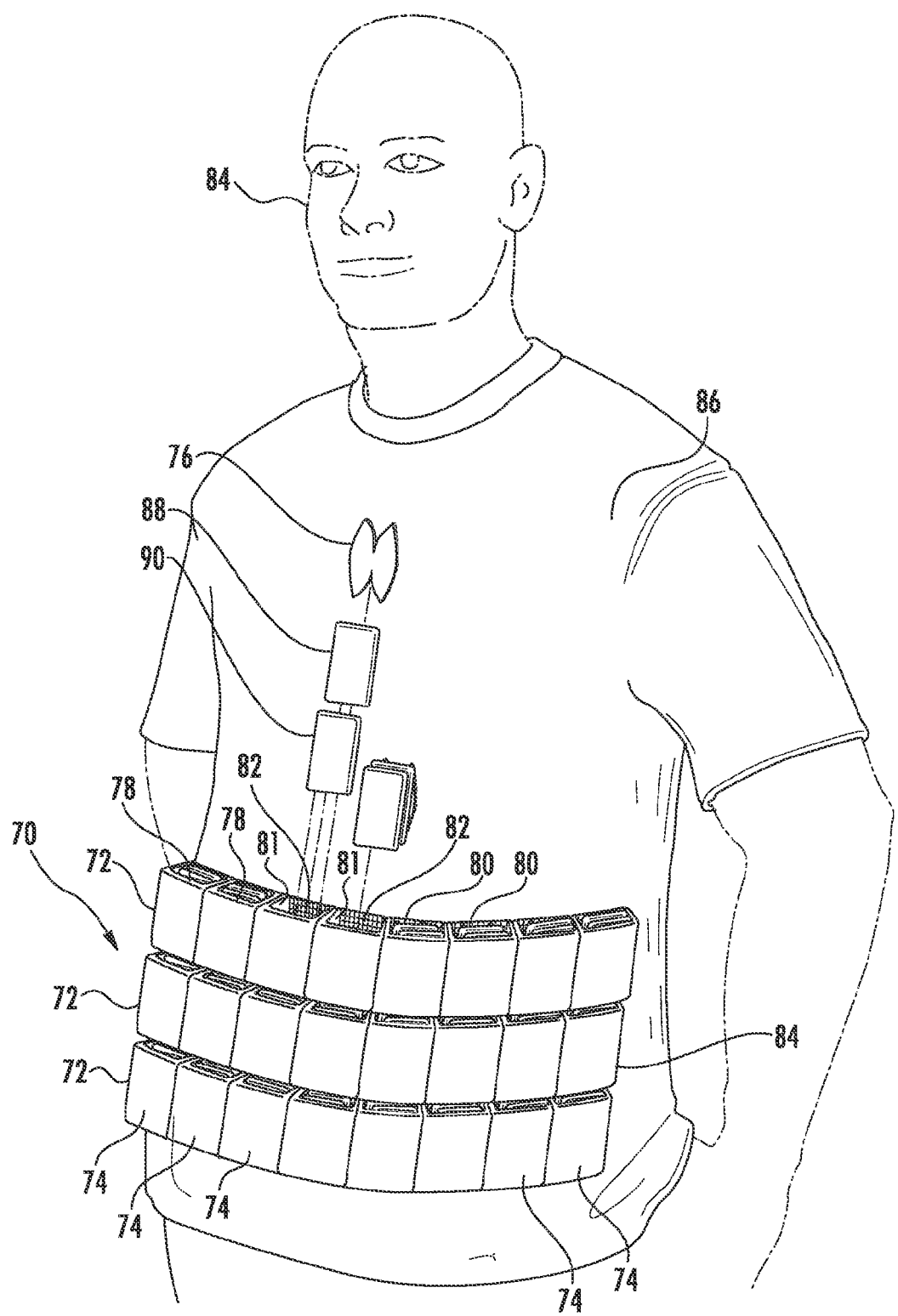
FIG. 6 is a partially exploded perspective view of an alternate embodiment of a weight reduction apparatus and a user, shown in phantom.

FIG. 6 shows an alternate embodiment of a weight reduction apparatus 70, which is substantially the same as the weight reduction apparatus 10, except that the weight reduction apparatus 70 has a plurality of receiving pocket topical applicator rows 72, each of which has a plurality of independent adjacent receiving pocket topical applicators 74.

Each of the receiving pocket topical applicators 74 of the plurality of receiving pocket topical applicator rows 72 is adapted to removably receive one or more natural plant products 76 and/or other suitable biodegradable weight loss products alone or in combination with one another.

Each of the plurality of receiving pocket topical applicators 74 has a frontal portion 78, side portions 80, an opening 81 adapted to removably receive the natural plant product 76 and/or other suitable biodegradable weight loss product, and a porous rear portion 82, which is typically of gauze-like material, mesh, screen-like material, or other suitable material, which allows the natural plant product 76 and/or other suitable biodegradable weight loss product to leach therethrough and be topically applied to a suitable are of user 84.

The weight reduction apparatus 70 may be worn by the user 84 with the porous rear portion 82 in contact with the user 84, alternatively over a shirt, garment, or other suitable material, or the weight reduction apparatus 70 may be fastened to or be an integral part of a shirt 86, as shown in FIG. 6, or garment or other suitable material that allows the natural plant product 76 and/or other suitable biodegradable weight loss product to leach therethrough and be topically applied to a suitable area of the user 84. The shirt 86, garment, or other suitable material may be, for example, gauze-like material, mesh, screen-like material, or other suitable material.

The weight reduction apparatus 70 may alternatively or additionally have a plurality of straps or other suitable fastening means adapted to removably fasten the weight reduction apparatus 70 to a suitable area of the user 84 or to the shirt, garment, or other suitable material. The porous rear portion 82 may optionally be an integral portion of the shirt, garment, or other suitable material.

Each of the plurality of receiving pocket topical applicators 74 also has a resiliently compressive material 88 adapted to press the natural plant product 76 and/or other suitable biodegradable weight loss product against the porous rear portion 82, and, thus, a suitable area of the user 84, and a waterproof material 90 adapted to minimize any juices from the natural plant products 76 and/or other suitable biodegradable weight loss products leaching through the frontal portion 76 of the receiving pocket topical applicators 74.

The receiving pocket topical applicators 74 are typically placed about the abdomen 92 of the user 84, although the receiving pocket topical applicators 74 may be placed about another suitable area.

Figure 7:
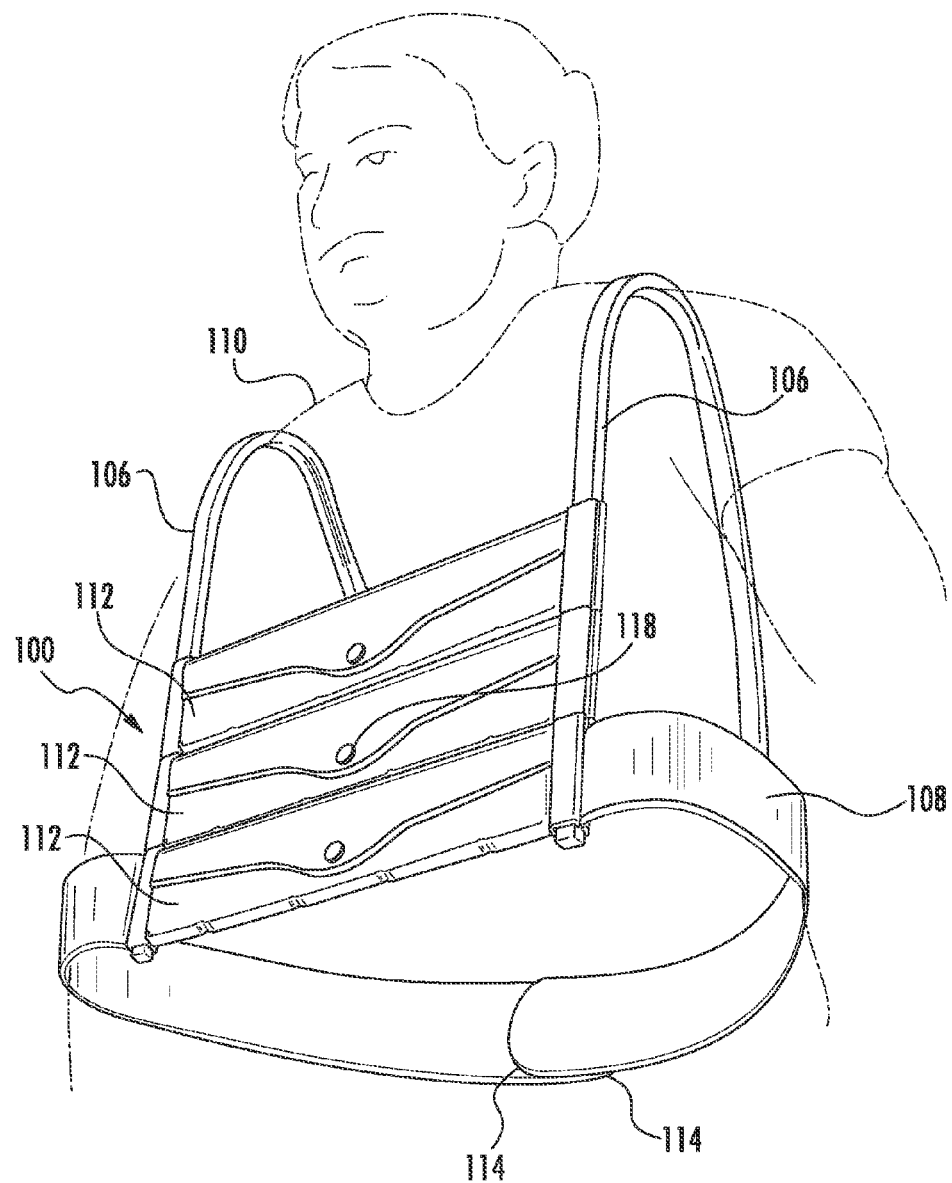
FIG. 7 is a perspective view of an alternate embodiment of a weight reduction apparatus and a user, shown in phantom.

FIG. 7 shows an alternate embodiment of a weight reduction apparatus 100, which is substantially the same as the weight reduction apparatus 10, except that the weight reduction apparatus 100 has opposing shoulder straps 106 and a belt 108 or other suitable fastening means adapted to removably fasten the weight reduction apparatus 100 to a user 110. The weight reduction apparatus 100 has a plurality of receiving pocket topical applicators 112 for removably receiving a natural plant product and/or other suitable biodegradable weight loss product alone or in combination with one another, The receiving pocket topical applicators 112 may be removably fastened to or removably mounted to the opposing shoulder straps 106 and/or the belt 108, which has releasable fastener ends 114 having hook and loop fasteners or other suitable releasable fasteners. The receiving pocket topical applicators 112 may also have optional releasable fasteners 118 for facilitating closure of the receiving pocket topical applicators 102.

Figure 8:
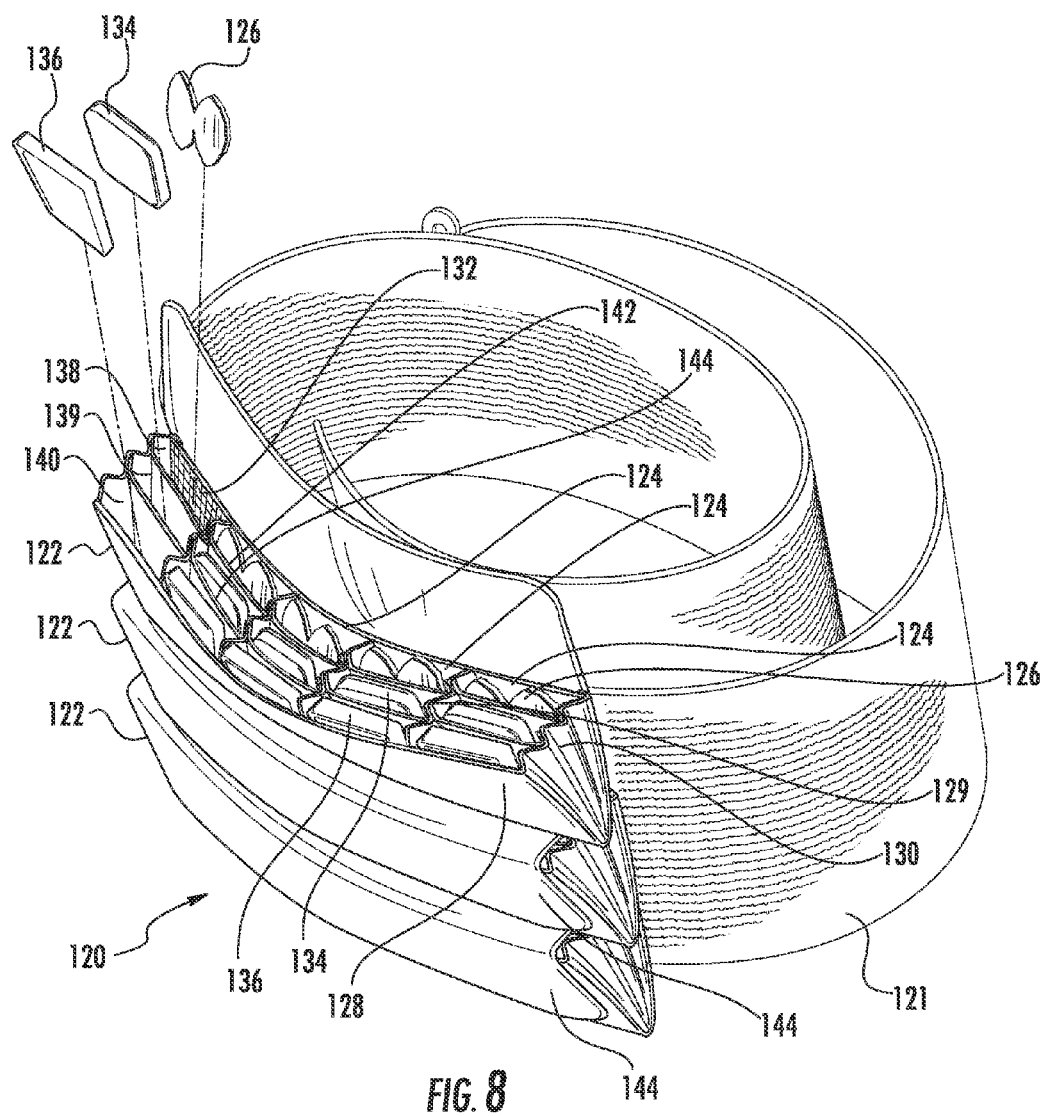
FIG. 8 is a partially exploded perspective view of an alternate embodiment of a weight reduction apparatus.
Figure 9:
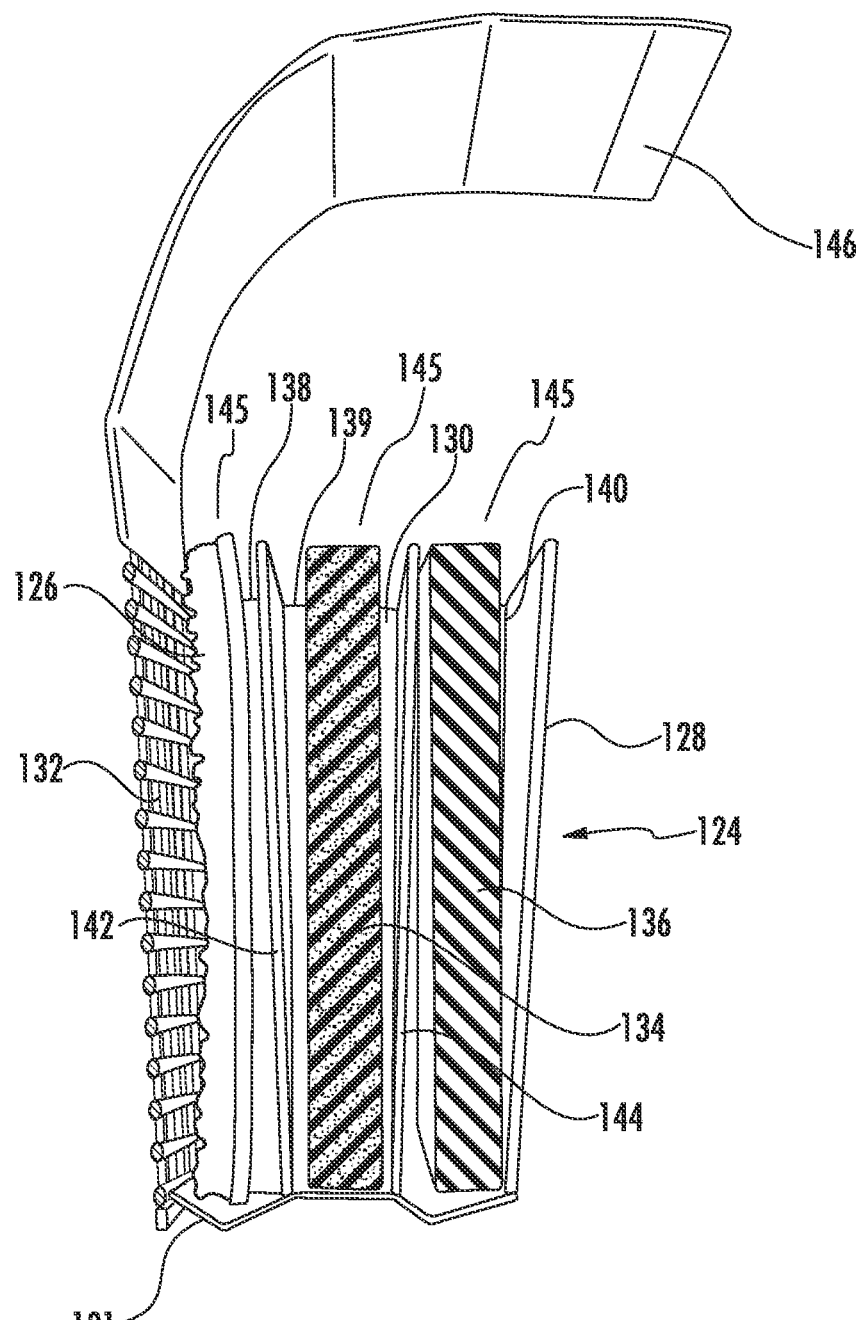
FIG. 9 is a side cross section view of the alternate embodiment of the weight reduction apparatus of FIG. 8.

FIGS. 8 and 9 show an alternate embodiment of a weight reduction apparatus 120, which is substantially the same as the weight reduction apparatus 10, except that the weight reduction apparatus 120 has a belt 121 or other suitable fastening means adapted to removably fasten the weight reduction apparatus 120 to a user. The weight reduction apparatus 120 has a plurality of receiving pocket applicator rows 122 having a plurality of receiving pocket topical applicators 124 for removably receiving a natural plant product 126 and/or other suitable biodegradable weight loss product alone or in combination with one another, Each of the receiving pocket topical applicators 124 has a frontal portion 128, side wall portions 129 and 130, a bottom 131, and a porous rear portion 132, as shown in FIGS. 8 and 9, which is typically of gauze-like material, mesh, screen-like material, or other suitable material, which allows the natural plant product 126 and/or other suitable biodegradable weight loss product to leach therethrough and be topically applied to a suitable area of a user.

Each of the plurality of receiving pocket topical applicators 124 also has a resiliently compressive material 134 adapted to press the natural plant product 126 and/or other suitable biodegradable weight loss product against the porous rear portion 132 and, thus, a suitable area of the user, and a waterproof material 136 adapted to minimize any juices from the natural plant product 126 and/or other suitable biodegradable weight loss products leaching through the frontal portion 128 of the receiving pocket topical applicators 124.

Each of the plurality of receiving pocket topical applicators 124 has a plurality of compartments 138, 139, and 140 adapted to separate or isolate the natural plant product 126 and/or other suitable biodegradable weight loss product from the resiliently compressive material 134 and the waterproof material 136, and also to separate the resiliently compressive material 134 from the waterproof material 136. The resiliently compressive material 134 and the waterproof material 136 are shown inserted into the compartments 139 and 140, respectively; however, the resiliently compressive material 134 and the waterproof material 136 may alternatively be inserted into the compartments 140 and 139, respectively, depending upon the needs of the user. The compartments 138, 139, and 140 are separated by interior walls 142 and 144, and have openings 145 adapted to removably receive the natural plant product 126 and/or other suitable biodegradable weight loss product, the resiliently compressive material 134 and the waterproof material 136. Each of the plurality of receiving pocket applicator rows 122 has a fold-over cover flap 146.

Figure 10:
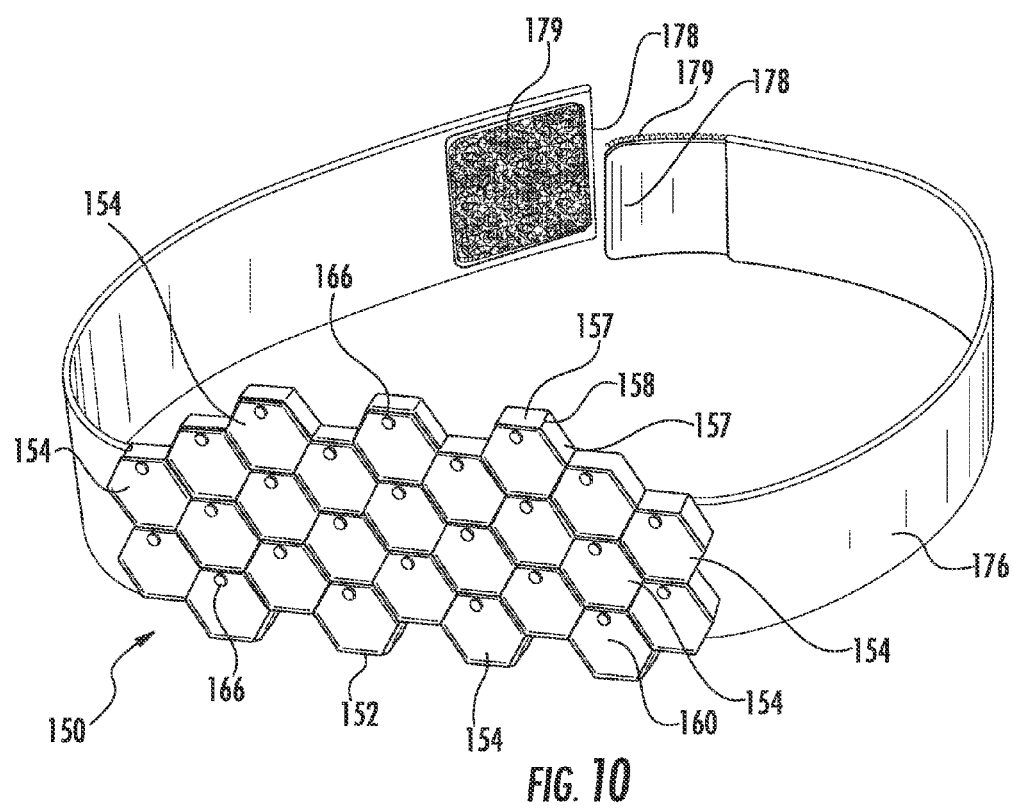
FIG. 10 is a perspective view of an alternate embodiment of a weight reduction apparatus.
Figure 11:
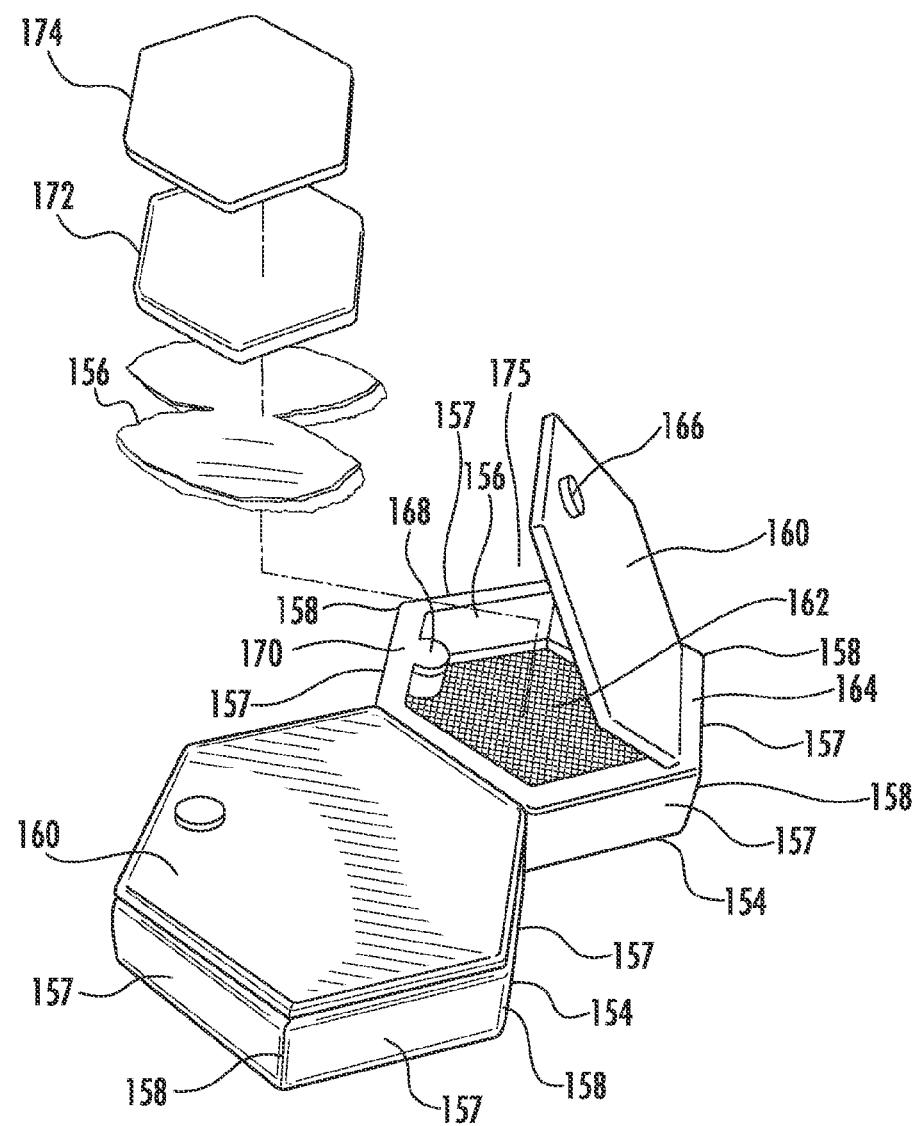
FIG. 11 is a partially exploded perspective view of a receiving compartment topical applicator of the alternate embodiment of the weight reduction apparatus of FIG. 10.

FIGS. 10 and 11 show an alternate embodiment of a weight reduction apparatus 150 having honeycomb array 152 of receiving compartment topical applicators 154 for removably receiving a natural plant product 156 and/or other suitable biodegradable weight loss product alone or in combination with one another. Each of the receiving compartment topical applicators 154 are hexagonal shaped, but may alternatively be another suitable polygon shape or another suitable shape, or a combination of suitable shapes may be used.

Each of the receiving compartment topical applicators 154 comprises a polygon like structure of side walls 157 adjoined at corner vertices 158, and has a hinged frontal portion 160 and a porous rear portion 162, which is typically of gauze-like material, mesh, screen-like material, or other suitable material, which allows the natural plant product 156 and/or other suitable biodegradable weight loss product to leach therethrough and be topically applied to a suitable area of a user.

The hinged frontal portion 160 is hingedly attached to an edge 164 of one of the side walls 157 preferably with a living hinge or other suitable hinge. Each of the receiving compartment topical applicators 154 may also have an optional button 166 to facilitate opening the receiving compartment topical applicator 154 and an optional releasable mating fastener 168 to facilitate and maintain closure of the hinged frontal portion 160 against edge 170 of another of the side walls 157.

Each of the receiving compartment topical applicators 154 also has a resiliently compressive material 172 adapted to press the natural plant product 156 and/or other suitable biodegradable weight loss product against the porous rear portion 162 and, thus, a suitable area of the user, and a suitable waterproof material 174, as shown in FIG. 11, adapted to minimize any juices from the natural plant product 156 and/or other suitable biodegradable weight loss product leaching out of the hinged frontal portion 160 of the receiving compartment topical applicators 154. Each of the receiving compartment topical applicators 154 has opening 175 is adapted to removably receive the natural plant product 156 and/or other suitable biodegradable weight loss product, the resiliently compressive material 172, and the waterproof material 174.

The receiving pocket topical applicators 154 are fastened or mounted to belt 176, as shown in FIG. 10, which has releasable fastener ends 178 having hook and loop fasteners 179 or other suitable releasable fasteners to fasten the belt 176 about a user. The belt 176 may have a portion thereof which is typically of gauze-like material, mesh, screen-like material, or other suitable material, which allows the natural plant product 156 and/or other suitable biodegradable weight loss product to leach therethrough and be topically applied to a suitable area of the user. The belt 176 may alternatively have a cut-out portion that allows the natural plant product 156 and/or other suitable biodegradable weight loss product to leach therethrough and be topically applied to a suitable area of the user.

The having honeycomb array 152 of the receiving compartment topical applicators 154 may be fastened to the belt 176 or optionally removably fastened or mounted to the belt 176 depending upon the needs of the user. The having honeycomb array 152 of the receiving compartment topical applicators 154 may alternatively be releasably fastened, mounted, or applies to the user by other suitable means.

Figure 12:
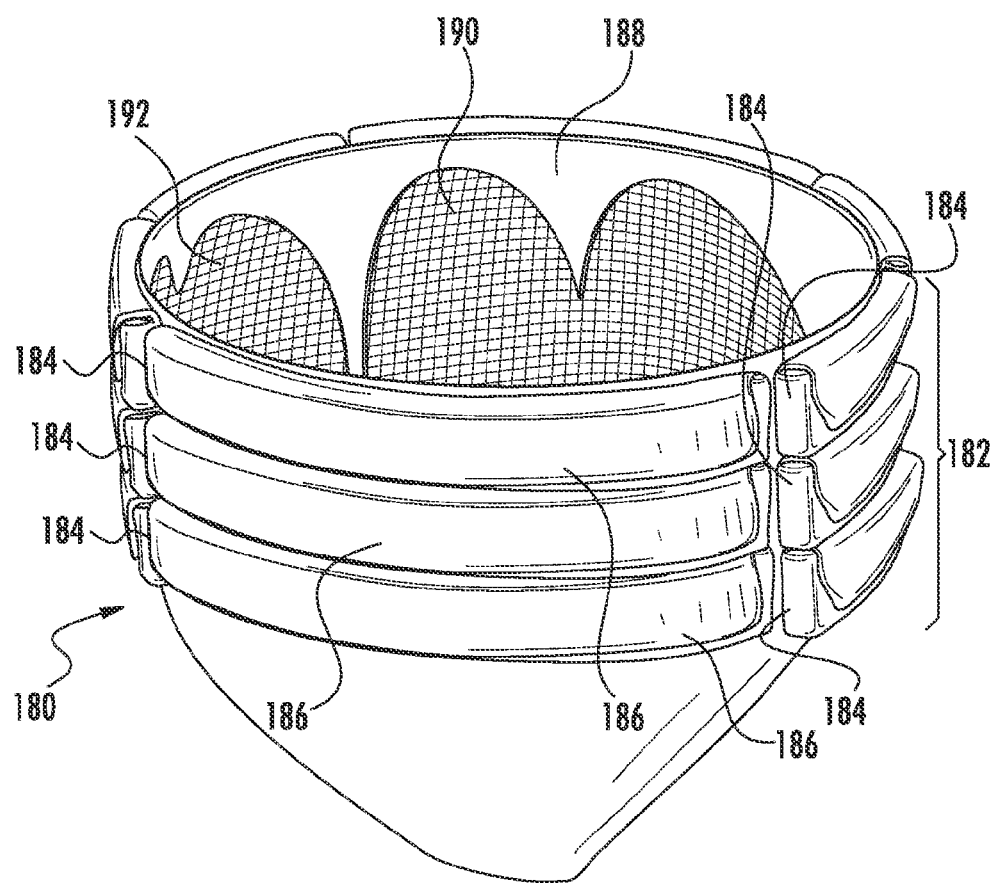
FIG. 12 is a perspective view of an alternate embodiment of a weight reduction apparatus.

FIG. 12 shows an alternate embodiment of a weight reduction apparatus 180 to be worn by a user. The weight reduction apparatus 180 has a plurality of groups 182 of rows 184 of receiving pocket topical applicators 186 for removably receiving a natural plant product and/or other suitable biodegradable weight loss product to leach therethrough and be topically applied to a suitable area of a user. The groups 182 of rows 184 of receiving pocket topical applicators 186 are fastened to or mounted to underpants 188, or a garment or other suitable material, such as for example, gauze-like material, mesh, screen-like material, or other suitable material.

The receiving pocket topical applicators 186 are typically placed about the abdomen, hips, and derriere or posterior of the user, although the receiving pocket topical applicators 186 may be placed about other suitable areas.

The underpants 188 of the weight reduction apparatus 180 has a porous rear portion 190, porous side portions 192, and porous front portion, each of which are typically of gauze-like material, screen-like material, or other suitable material, which allows juices of the natural plant product to leach therethrough and be topically applied to a suitable area of the user.

Figure 13:
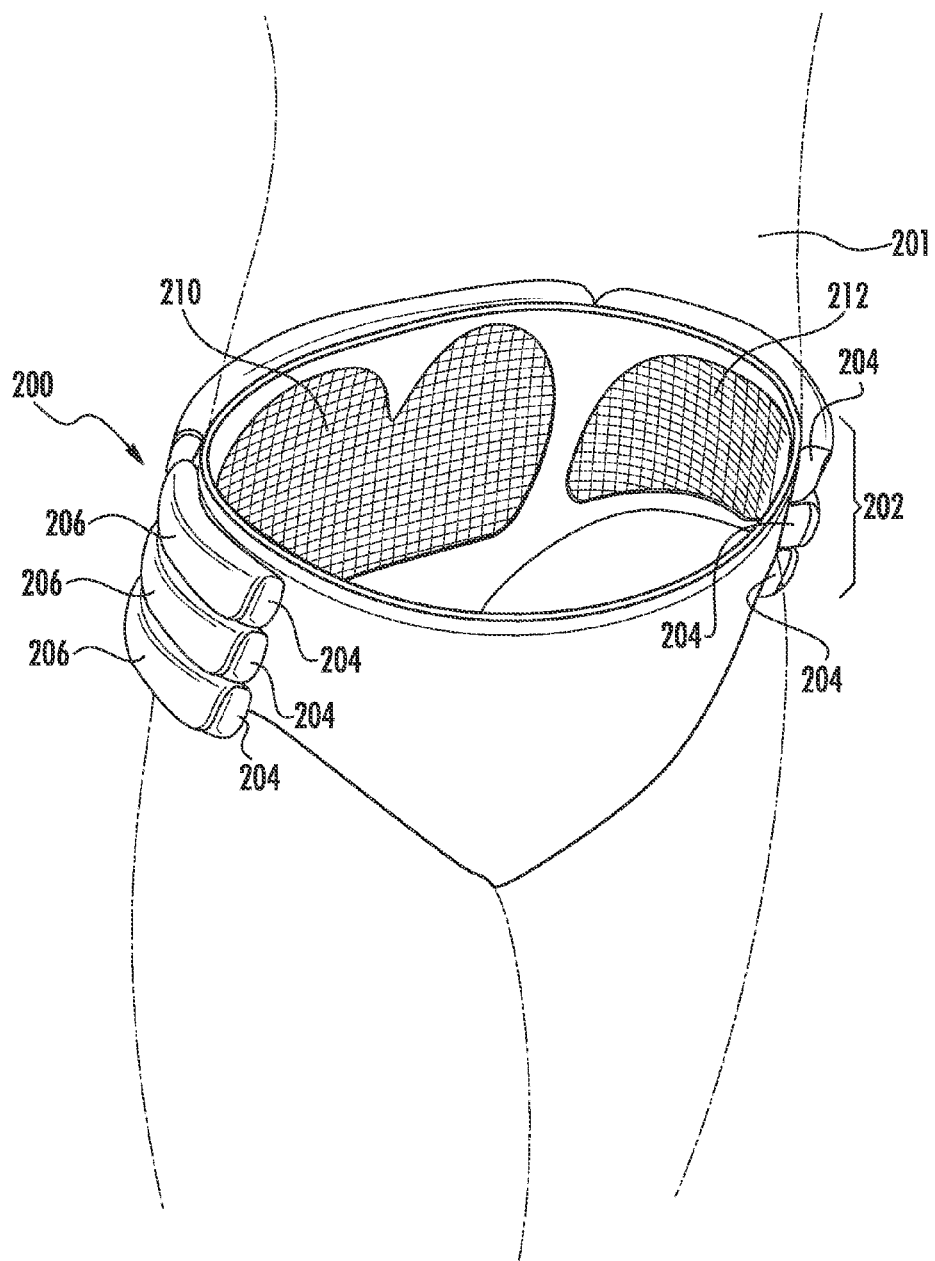
FIG. 13 is a perspective view of an alternate embodiment of a weight reduction apparatus and a user, shown in phantom.

FIG. 13 shows an alternate embodiment of a weight reduction apparatus 200 to be worn by a user 201. The weight reduction apparatus 200 has a plurality of groups 202 of rows 204 of receiving pocket topical applicators 206 for removably receiving a natural plant product and/or other suitable biodegradable weight loss product to leach therethrough and be topically applied to a suitable area of the user 201. The groups 202 of rows 204 of receiving pocket topical applicators 206 are fastened to or mounted to underpants 208, or a garment or other suitable material, such as for example, gauze-like material, mesh, screen-like material, or other suitable material.

The receiving pocket topical applicators 206 are typically placed about the hips and derriere or posterior of the user, although the receiving pocket topical applicators 206 may be placed about other suitable areas.

The underpants 208 of the weight reduction apparatus 200 has a porous rear portion 210 and porous side portions 212, each of which are typically of gauze-like material, screen-like material, or other suitable material, which allows natural plant product to leach therethrough and be topically applied to a suitable area of the user 201.

Figure 14:
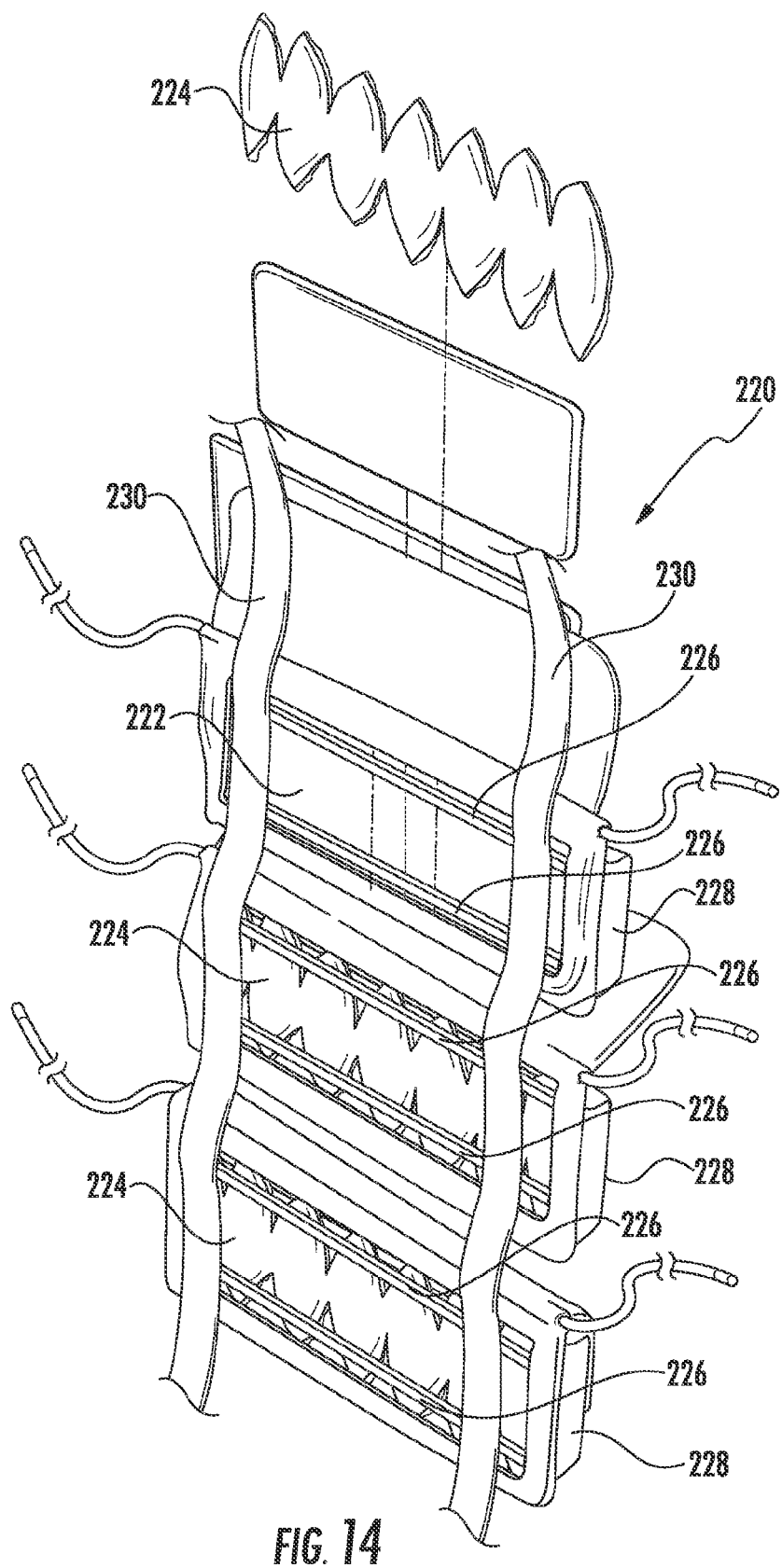
FIG. 14 is a partially exploded rear perspective view of an alternative embodiment of a weight reduction apparatus.
Figure 15:
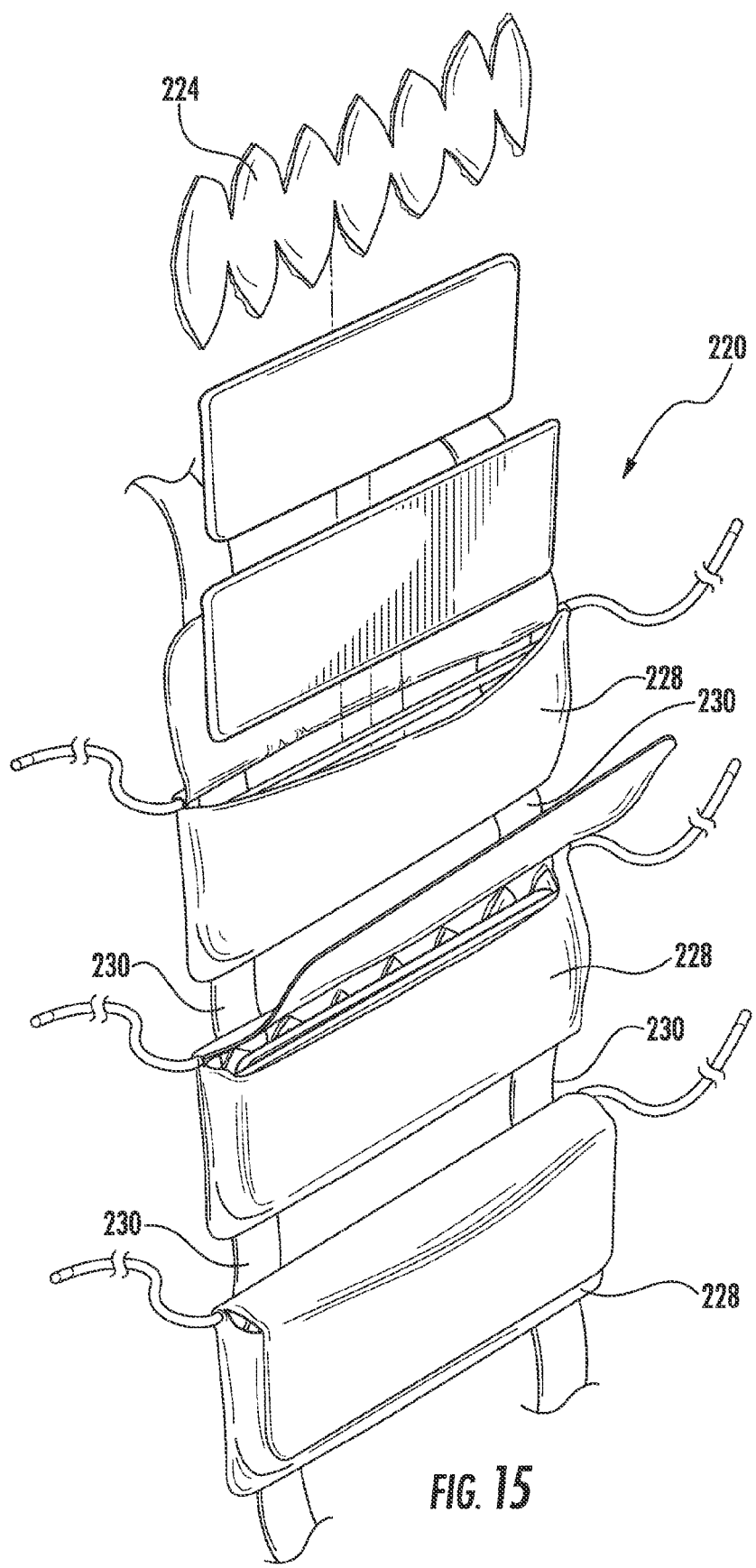
FIG. 15 is a partially exploded front perspective view of the alternative embodiment of the weight reduction apparatus of FIG. 14.
Figure 16:
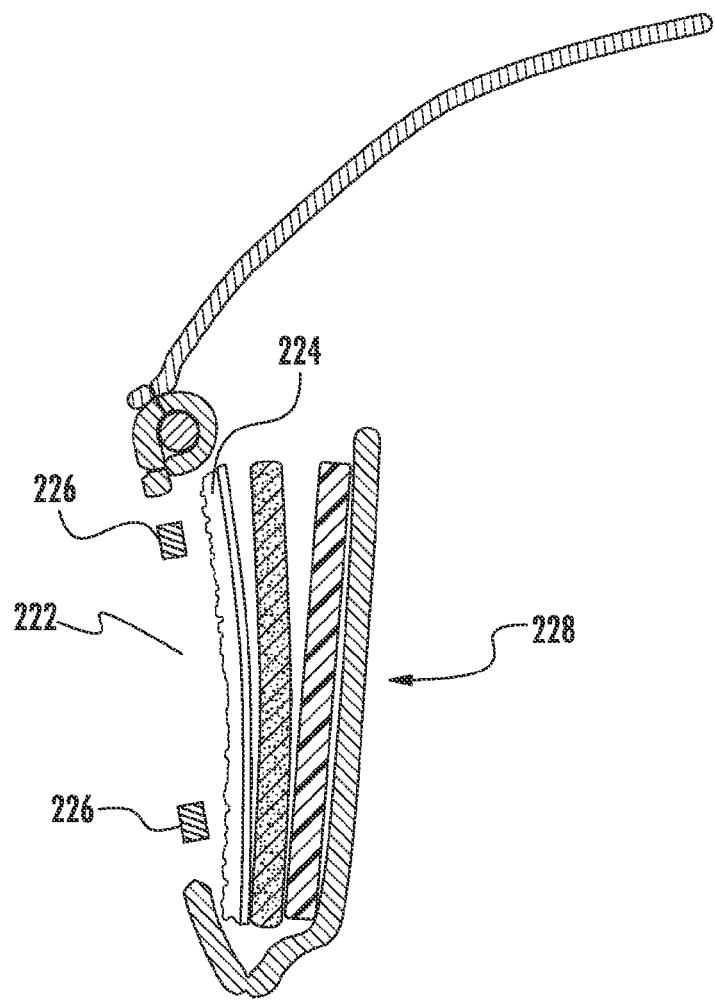
FIG. 16 is a side cross section view of a receiving pocket topical applicator of the weight reduction apparatus of FIG. 14.

FIGS. 14-16 show an alternate embodiment of a weight reduction apparatus 220, which is substantially the same as the weight reduction apparatus 10, except that the weight reduction apparatus 220 has rear openings 222 adapted to facilitate direct contact of natural plant product 224 and/or other suitable biodegradable weight loss product with a user, reinforcing stays 226 adapted to reinforce each of a plurality of receiving pocket topical applicators 228, and opposing straps 230 adapted to separate the receiving pocket topical applicators 228 one from the other.

FIG. 17 shows an alternate embodiment of a weight reduction apparatus 250 which may be removably fastened to a sheet 252 or covering of a mattress 254, which a user may sleep on or rest on and topically apply a natural plant product 256 and/or other suitable biodegradable weight loss product to a suitable area of the user. The weight reduction apparatus 250 has a plurality of receiving pocket topical applicators 258 for removably receiving a natural plant product 256 and/or other suitable biodegradable weight loss product alone or in combination with one another. Each of the receiving pocket topical applicators 258 has a porous top portion 260, which is typically of gauze-like material, mesh, screen-like material, or other suitable material, which allows juices of the natural plant product 256 and/or other suitable biodegradable weight loss product to leach therethrough and be topically applied to a suitable area of a user.

The receiving pocket topical applicators 258 are fastened or mounted to a waterproof material 262 to prevent juices from the natural plant product 256 and/or other suitable biodegradable weight loss product from damaging the sheet 252 or covering of the mattress 254.

The weight reduction apparatus 250 may be removably fastened to the sheet 252 or covering of the mattress 254 with opposing hook and loop fasteners 264 and 266, which are fastened to the waterproof material 262 and the sheet 252 or covering of the mattress 254.

Although the present invention has been described in considerable detail with reference to certain preferred versions thereof, other versions are possible. Therefore, the spirit and scope of the appended claims should not be limited to the description of the preferred versions contained herein.

What is claimed is:

1. A method for applying a plant product, comprising:
   applying a portion of a plant product to the epidermis of a human with an apparatus;
   wherein the apparatus is removably fastened with a belt or straps to a human body, and wherein the apparatus comprises:

the belt or straps and a plurality of pockets or containers containing a plant product; wherein each pocket or container comprises a frontal portion and a porous rear portion in contact with the epidermis; wherein the porous rear portion is made of a material selected from gauze, mesh, or screen and wherein the porous rear portion allows the portion of the plant product to leach from the pocket or container through the material to the epidermis, and wherein the frontal portion comprises a waterproof material to minimize juices from the plant product leaching through the frontal portion; and wherein the plant product is selected from tomato, potato and mixtures thereof.

2. The method of claim 1, wherein the plant product is tomato.

3. The method of claim 2, wherein the tomato is green tomato.

4. The method of claim 1, wherein the plant product is potato.

5. The method of claim 1, wherein the plant product comprises a mixture of tomato and potato.

6. The method of claim 1, wherein the tomato is green tomato.

7. The method of claim 1, wherein the applying is repeated.

8. The method of claim 1, wherein the epidermis is an epidermal layer external to adipose tissue.

9. The method of claim 8, wherein the epidermal layer is an epidermal layer of the abdomen.

10. The method of claim 1, wherein the belt or straps comprise releasable fastening ends.

11. The method of claim 1, wherein the plant product contained in the plurality of pockets or containers is cut open to reveal the inner portion of the plant product.

12. The method of claim 1, wherein the plurality of pockets or containers comprise releasable fasteners for closing the individual pockets or containers.

13. The method of claim 1, wherein the apparatus is removably held in place adjacent the epidermis of the human body.

14. A method for applying a plant product, comprising:
applying a portion of a plant product to theepidermis of a human with an apparatus;
wherein the apparatus is removably fastened with a belt or straps to a human body, and wherein the apparatus comprises:
the belt or straps and
a plurality of pockets or containers containing a plant product; wherein each pocket or container comprises a frontal portion and a porous rear portion in contact with the epidermis; wherein the porous rear portion is made of a material selected from gauze, mesh, or screen and wherein the porous rear portion allows the portion of the plant product to leach from the pocket or container through the material to the epidermis, and wherein the frontal portion comprises a waterproof material to minimize juices from the plant product leaching through the frontal portion; and wherein the plant product comprises tomato.

15. The method of claim 14, wherein the tomato is green tomato.

16. The method of claim 14, wherein the plant product contained in the plurality of pockets or containers is cut open to reveal the inner portion of the plant product.

17. A method for applying a plant product, comprising:
applying a portion of a plant product to the epidermis of a human with an apparatus;
wherein the apparatus is removably fastened with a belt or straps to a human body, and wherein the apparatus comprises:
the belt or straps and
a plurality of pockets or containers containing a plant product; wherein each pocket or container comprises a frontal portion and a porous rear portion in contact with the epidermis; wherein the porous rear portion is made of a material selected from gauze, mesh, or screen and wherein the porous rear portion allows the portion of the plant product to leach from the pocket or container through the material to the epidermis, and wherein the frontal portion comprises a waterproof material to minimize juices from the plant product leaching through the frontal portion; and wherein the plant product is potato.

18. The method of claim 17, wherein the plant product contained in the plurality of pockets or containers is cut open to reveal the inner portion of the plant product.

19. A method for applying a plant product, comprising:
applying a portion of a plant product to the epidermis of a human with an apparatus;
wherein the apparatus is removably fastened with a belt or straps to a human body, and wherein the apparatus comprises:
the belt or straps and
a plurality of pockets or containers containing a plant product; wherein each pocket or container comprises a frontal portion and a porous rear portion in contact with the epidermis; wherein the porous rear portion is made of a material selected from gauze, mesh, or screen and wherein the porous rear portion allows the portion of the plant product to leach from the pocket or container through the material to the epidermis, and wherein the frontal portion comprises a waterproof material to minimize juices from the plant product leaching through the frontal portion; and wherein the plant product comprises a mixture of potato and tomato.

20. The method of claim 19 wherein the tomato is green tomato.

21. The method of claim 19, wherein the plant product contained in the plurality of pockets or containers is cut open to reveal the inner portion of the plant product.

* * * * *